US012753425B2

(12) United States Patent
Vojinovic et al.

(10) Patent No.: US 12,753,425 B2
(45) Date of Patent: Oct. 6, 2026

(54) METHOD OF PRODUCING ALLOLACTOSE

(71) Applicant: Chr. Hansen A/S, Hoersholm (DK)

(72) Inventors: Vojislav Vojinovic, Hoersholm (DK); Kim Ib Soerensen, Hoersholm (DK); Laurent Guinot, Arpajon (FR)

(73) Assignee: Chr. Hansen A/S, Hoersholm (DK)

( * ) Notice: Subject to any disclaimer, the term of this patent is extended or adjusted under 35 U.S.C. 154(b) by 332 days.

(21) Appl. No.: 18/546,949

(22) PCT Filed: Feb. 22, 2022

(86) PCT No.: PCT/EP2022/054396
§ 371 (c)(1),
(2) Date: Aug. 17, 2023

(87) PCT Pub. No.: WO2022/180034
PCT Pub. Date: Sep. 1, 2022

(65) Prior Publication Data

US 2024/0287565 A1 Aug. 29, 2024

(30) Foreign Application Priority Data

Feb. 26, 2021 (EP) .................................... 21159604

(51) Int. Cl.

| | |
|---|---|
| ***C12P 19/12*** | (2006.01) |
| ***A23C 9/123*** | (2006.01) |
| ***C12N 1/20*** | (2026.01) |
| ***C12N 9/12*** | (2006.01) |
| ***C12R 1/46*** | (2006.01) |

(52) U.S. Cl.
CPC ............ *C12P 19/12* (2013.01); *A23C 9/1238* (2013.01); *C12N 1/20* (2013.01); *C12N 9/1205* (2013.01); *C12R 2001/46* (2021.05); *C12Y 207/01002* (2013.01); *C12Y 207/01006* (2013.01)

(58) Field of Classification Search
CPC ......... C12P 19/12; A23C 9/1238; C12N 1/20; C12N 9/1205; C12R 2001/46; C12Y 207/01002; C12Y 207/01006
See application file for complete search history.

(56) References Cited

U.S. PATENT DOCUMENTS

| | | | | |
|---|---|---|---|---|
| 10,813,367 | B2 | 10/2020 | Garrigues et al. | |
| 2015/0086675 | A1* | 3/2015 | Johansen ............ | C12N 15/746 506/10 |

FOREIGN PATENT DOCUMENTS

| | | | |
|---|---|---|---|
| EP | 2 957 180 | A1 | 3/2018 |
| EP | 3 620 510 | A1 | 3/2020 |
| WO | 2013160413 | A1 | 10/2013 |
| WO | 2015193459 | A1 | 12/2015 |
| WO | 2017103051 | A1 | 6/2017 |
| WO | 2018177835 | A1 | 10/2018 |

OTHER PUBLICATIONS

Toba et al. Allolactose and 6-0-β-D-Galactopyranosyl-D-Galactose in Commercial Yogurt, Journal of Dairy Science vol. 65, Issue 5, May 1982, p. 702-706 (Year: 1982).*
Jorgensen et al. Processing of high-protein yoghurt—A review, International Dairy Journal, vol. 88, Jan. 2019, p. 42-59 (Year: 2019).*
U.S. Appl. No. 18/546,950, filed Aug. 17, 2023, Broend et al.
Iskandar, Christelle F. et al.; "Review of lactose and galactose metabolism in Lactic Acid Bacteria dedicated to expert genomic annotation"; Trends in Food Science & Technology, vol. 88; Mar. 26, 2019; pp. 121-132.
Kremling, A. et al.; "Metabolic networks: biology meets engineering sciences"; Topics in Current Genetics, vol. 13; Jul. 6, 2005; pp. 215-234.
SØrensen, Kim I., et al.; "Enhancing the Sweetness of Yoghurt through Metabolic Remodeling of Carbohydrate Metabolism in *Streptococcus thermophilus* and *Lactobacillus delbrueckii* subsp. *bulgaricus*"; Applied and Environmental Microbiology, vol. 82, No. 12; Apr. 22, 2016; pp. 3683-3692.

* cited by examiner

*Primary Examiner* — Robert B Mondesi
*Assistant Examiner* — Naghmeh Nina Moazzami
(74) *Attorney, Agent, or Firm* — Yoshimi D. Barron

(57) ABSTRACT

The invention relates to a method of obtaining a composition comprising allolactose by a applying one or more glucose-deficient lactic acid bacteria strains. The invention also relates to the use of said strains for the preparation of a food product comprising allolactose and to the use of said strains for increasing the content of allolactose in a food product. The invention also relates to a food product comprising allolactose and one or more glucose-deficient lactic acid bacteria strains.

12 Claims, No Drawings

METHOD OF PRODUCING ALLOLACTOSE

CROSS-REFERENCE TO RELATED APPLICATIONS

The present application is the U.S. National Stage of International Application No. PCT/EP2022/054396, filed Feb. 22, 2022, and claims priority to European Patent Application No. 21159604.4, filed Feb. 26, 2021.

TECHNICAL FIELD OF THE INVENTION

The invention relates to a method of producing allolactose.

BACKGROUND OF THE INVENTION

Functional and healthy foods and their impact on for example the gut microbiota are increasingly receiving attention from the global consumer.

Functional foods can be defined as dietary items that, besides providing nutrients and energy, beneficially modulate one or more targeted functions in the body, by enhancing a certain physiological response and/or by reducing the risk of disease (Nicoletti, 2012).

Notable properties of the gut microbiota include its functionality and resilience. Several strategies have been proposed to modulate the composition and/or function of the gut microbiota. One such strategy is to apply functional foods such probiotics and other live microorganisms, prebiotics and synbiotics to modulate the composition and/or function of the gut microbiota. The current scientific definition of a prebiotic is: “a substrate that is selectively utilized by host microorganisms conferring a health benefit”. Thus, the concept includes three essential parts: a substance, a physiologically beneficial effect, and a mechanism.

Galactooligosaccharides (GOS) nondigestible fiber with prebiotic activity. They are nondigestible oligosaccharides and are comprised of 2 to 20 molecules of galactose and 1 molecule of glucose. GOS are recognized as important prebiotics for their stimulation of the proliferation of intestinal lactic acid bacteria and bifidobacteria. Therefore, they beneficially affect the host by selectively stimulating the growth and/or activity of a number of gastrointestinal microbes (probiotics) that confer health benefits. GOS have proven to be useful for the modulation of the colonic microbiota toward a healthy balance, which usually involves the increase of bifidobacteria and lactic acid bacteria and the decrease of less desirable microorganisms.

Allolactose is a disaccharide similar to lactose and is considered a common GOS. It consists of the monosaccharides D-galactose and D-glucose linked through a β1-6 glycosidic linkage instead of the β1-4 linkage of lactose. Allolactose may arise from transglycosylation of lactose by β-galactosidase.

In view of the high demand for functional and healthy food by the global consumers, there is a growing commercial interest in the food industry for producing GOSs such as allolactose as a functional ingredient for a wide range of products and especially fresh dairy products.

The production of allolactose itself is important to the industry however, there is an even greater demand for e.g. fresh dairy products where allolactose is not actively added to the product but where allolactose is in fact produced directly in the product. In addition to food products such as fresh dairy products comprising GOS, healthy food products also include low-calorie sweet-tasting food products.

Sugar in e.g. fermented food products such as fresh dairy products is more often being replaced with sweeteners such as aspartame, acesulfame K, sucralose and saccharin which can provide the sweetness with a lower intake of calories. During recent years consumer awareness on the drawbacks of artificial sweeteners have increased the demand for fermented milk products which only contain natural sweeteners or, preferably, contain no added sweetener. A special challenge lies in developing food products such as fresh dairy products where the natural (inner) sweetness is high Based on the above, there is a need to provide methods by which it is possible to obtain fermented food products such as fresh dairy products that simultaneously comprises (i) allolactose and (ii) increased natural sweetness and wherein the allolactose content and the increased natural sweetness is primarily generated directly in the product during fermentation.

SUMMARY OF THE INVENTION

The above objects are achieved by the present invention as it among others provides a method for obtaining a composition comprising allolactose by use of at least one or more glucose-deficient lactic acid bacteria strains. The invention also provides a method of obtaining a composition such as a fermented food product and in particular fresh dairy product comprising allolactose by using said strains. Also, the invention relates to a composition comprising allolactose and said stains and well as a method for increasing the content of allolactose in a composition using said strains.

Thus, in one aspect the invention relates to a method for producing a composition comprising allolactose, said method comprising the steps:

a) inoculating a substrate comprising lactose with one or more glucose-deficient lactic acid bacteria strains, wherein the glucose-deficiency of said strains is caused by a mutation in the DNA sequence of the glcK gene encoding a glucokinase protein; and
b) fermenting said inoculated substrate to obtain a composition comprising allolactose.

In a further aspect the present invention relates to a composition comprising allolactose obtained by the method according to the present invention.

Yet an aspect of the present invention relates to a composition comprising at least 0.04% w/w allolactose, wherein said composition further comprises one or more glucose-deficient lactic acid bacteria strains, wherein the glucose-deficiency of said strains is caused by a mutation in the DNA sequence of the glcK gene encoding a glucokinase protein.

Another aspect of the present invention relates to the use of one or more glucose-deficient lactic acid bacteria strains for the preparation of a composition comprising allolactose, and wherein the glucose-deficiency of said strains is caused by a mutation in the DNA sequence of the glcK gene encoding a glucokinase protein.

A further aspect of the present invention relates to the use of one or more glucose-deficient lactic acid bacteria strains for increasing the content of allolactose in a composition, and wherein the glucose-deficiency of said strains is caused by a mutation in the DNA sequence of the glcK gene encoding a glucokinase protein.

DETAILED DESCRIPTION OF THE INVENTION

Prior to outlining the present invention in more details, a set of terms and conventions is first defined:

The term "genus" means genus as defined on the website: www.ncbi.nlm.nih.gov/taxonomy. A bacterial "strain" as used herein refers to a bacterium which remains genetically unchanged when grown or multiplied. A multiplicity of identical bacteria are included.

In the present context, the term "mutant" or "mutant strain" should be understood as a strain derived, or a strain which can be derived, from a strain of the invention (or the mother strain) by means of e.g. genetic engineering, radiation and/or chemical treatment. It is preferred that the mutant is a functionally equivalent mutant, e.g. a mutant that has substantially the same, or improved, properties (e.g. regarding texture, shear stress, viscosity, gel firmness, mouth coating, flavor, post acidification, acidification speed, and/or phage robustness) as the strain from which it is derived. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant, less than 5%, or less than 1% or even less than 0.1% of the nucleotides in the bacterial genome have been shifted with another nucleotide, or deleted, compared to the mother strain. As will be clear to the skilled person mutants of the present invention can also be mother strains.

In the present context, the term "variant" or "variant strain" should be understood as a strain which is functionally equivalent to a strain of the invention, e.g. having substantially the same, or improved, properties or characteristics e.g. texture, acidification speed, viscosity, gel firmness, mouth coating, flavor, post acidification and/or phage robustness). Such variants, which may be identified using appropriate screening techniques, are a part of the present invention.

For purposes of the present invention, the degree of identity between two amino acid sequences is determined using the Needleman-Wunsch algorithm (Needleman and Wunsch (1970) J. Mol. Biol. 48: 443-453) as implemented in the Needle program of the EMBOSS package (EMBOSS: The European Molecular Biology Open Software Suite, Rice et al. (2000) Trends in Genetics 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labelled "longest identity" (obtained using the –no brief option) is used as the percent identity and is calculated as follows: (Identical Residues×100)/(Length of Alignment−Total Number of Gaps in Alignment)

In the present description and claims the conventional one-letter and three-letter codes for amino acid residues are used. For ease of reference, amino acid changes in mutants and variants of the invention are described by use of the following nomenclature: amino acid residue in the parent enzyme; position; substituted amino acid residue(s). According to this nomenclature, the substitution of, for instance, an alanine residue for a glycine residue at position 20 is indicated as Ala20Gly or A20G. The deletion of alanine in the same position is shown as Ala20* or A20*. The insertion of an additional amino acid residue (e.g. a glycine) is indicated as Ala20AlaGly or A20AG. The deletion of a consecutive stretch of amino acid residues (e.g. between alanine at position 20 and glycine at position 21) is indicated as DELTA(Ala20-Gly21) or DELTA(A20-G21). When a parent enzyme sequence contains a deletion in comparison to the enzyme sequence used for numbering an insertion in such a position (e.g. an alanine in the deleted position 20) is indicated as *20Ala or *20A. Multiple mutations are separated by a plus sign or a slash. For example, two mutations in positions 20 and 21 substituting alanine and glutamic acid for glycine and serine, respectively, are indicated as A20G+E21S or A20G/E21S. When an amino acid residue at a given position is substituted with two or more alternative amino acid residues these residues are separated by a comma or a slash. For example, substitution of alanine at position 30 with either glycine or glutamic acid is indicated as A20G,E or A20G/E, or A20G, A20E. When a position suitable for modification is identified herein without any specific modification being suggested, it is to be understood that any amino acid residue may be substituted for the amino acid residue present in the position. Thus, for instance, when a modification of an alanine in position 20 is mentioned but not specified, it is to be understood that the alanine may be deleted or substituted for any other amino acid residue (i.e. any one of R, N, D, C, Q, E, G, H, I, L, K, M, F, P, S, T, W, Y, V).

In the context of the present invention, a mutation in the gene (gene mutation) is to be understood as an alteration in the nucleotide sequence of the genome of an organism resulting in changes in the phenotype of said organism, wherein the alteration may be a deletion of a nucleotide, a substitution of a nucleotide by another nucleotide, an insertion of a nucleotide, or a frameshift. In the context of the present invention, a deletion is to be understood as a genetic mutation resulting in the removal of one or more nucleotides of a nucleotide sequence of the genome of an organism; a insertion is to be understood as the addition of one or more nucleotides to the nucleotide sequence; a substitution (or point mutation) is to be understood as a genetic mutation where a nucleotide of a nucleotide sequence is substituted by another nucleotide; a frameshift is to be understood as a genetic mutation caused by a insertion or deletion of a number of nucleotides in a nucleotide sequence that is not divisible by three, therefore changing the reading frame and resulting in a completely different translation from the original reading frame; an introduction of a stop codon is to be understood as a point mutation in the DNA sequence resulting in a premature stop codon; a inhibition of substrate binding of the encoded protein is to be understood as any mutation in the nucleotide sequence that leads to a change in the protein sequence responsible for preventing binding of a substrate to its catalytic site of the protein. Furthermore, a knockout mutant is to be understood as genetic mutation resulting in the removal or deletion of a gene, such as an entire gene or an entire open reading frame from the genome of an organism.

In the present description and claims the conventional one-letter code for nucleotides is used following the analogous principles as described for amino acids nomenclature supra.

Algorithms for aligning sequences and determining the degree of sequence identity between them are well known in the art. For the purpose of the present invention a process may be carried out for aligning nucleotide sequences using blastn as provided by the National Center for Biotechnology Information (NCBI) on https://blast.ncbi.nlm.nih.gov applying standard parameter.

A "mutant bacterium" or a "mutant strain" as used herein refers to a natural (spontaneous, naturally occurring) mutant bacterium or an induced mutant bacterium comprising one or more mutations in its genome (DNA) which are absent in the wild type DNA. An "induced mutant" is a bacterium where the mutation was induced by human treatment, such as treatment with chemical mutagens, UV- or gamma radiation etc. In contrast, a "spontaneous mutant" or "naturally occurring mutant" has not been mutagenized by man. Mutant bacteria are herein, non-GMO (non-genetically modified organism), i.e. not modified by recombinant DNA technology.

Allolactose is to be understood as a disaccharide that consists of the monosaccharides D-galactose and D-glucose linked through a β1-6 glycosidic linkage.

The amount of fructose, galactose, glucose, sucrose, lactose and allolactose is measured as disclosed in Example 1.

In connection with strains of the genus *Lactobacillus*, the term "CFU" means colony forming units as determined by growth (forming a colony) on an MRS agar plate incubated at anaerobic conditions at 37° C. for 3 days. The MRS agar has the following composition (g/l):

Bacto Proteose Peptone No. 3: 10.0
Bacto Beef extract: 10.0
Bacto Yeast extract: 5.0
Dextrose: 20.0
Sorbitan Monooleate Complex: 1.0
Ammonium Citrate: 2.0
Sodium Acetate: 5.0
Magnesium Sulfate: 0.1
Manganese Sulfate: 0.05
Potassium Phosphate Dibasis: 2.0
Bacto Agar: 15.0
Milli-Q water: 1000 ml.
pH is adjusted to 5.4 or 6.5: pH is adjusted to 6.5 for *L. rhamnosus, L. casei* and *L. paracasei*. For all other *Lactobacillus* species the pH is adjusted to 5.4. In particular, pH is adjusted to 5.4 for *L. delbrueckii* subsp. *bulgaricus; L. acidophilus* and *L. helveticus*. pH is adjusted to 6.5 for *L. rhamnosus, L. casei* and *L. paracasei.*

In connection with *S. thermophilus*, the term "CFU" means colony forming units as determined by growth (forming a colony) on an M 17 agar plate incubated at aerobic conditions at 37° C. for 3 days. The M 17 agar has the following composition (g/l):

Tryptone: 2.5 g
Peptic digest of meat: 2.5 g
Papaic digest of soybean meal: 5.0 g
Yeast extract: 2.5 g
Meat extract: 5.0 g
Lactose: 5.0 g
Sodium-glycero-phosphate: 19.0 g
Magnesium sulphate, 7 $H_2O$: 0.25 g
Ascorbic acid: 0.5 g
Agar: 15.0 g
Milli-Q water: 1000 ml.
pH is adjusted to final pH 7.1±0.2 (25° C.)

As used herein, the term "lactic acid bacterium" designates a gram-positive, mi-croaerophilic or anaerobic bacterium, which ferments sugars with the production of acids including lactic acid as the predominantly produced acid, acetic acid and propionic acid.

The industrially most useful lactic acid bacteria are found within the order "Lactobacillales" which includes *Lactococcus* spp., *Streptococcus* spp., *Lactobacillus* spp., *Leuconostoc* spp., *Pediococcus* spp., *Brevibacterium* spp., *Enterococcus* spp. and *Propionibacterium* spp. Lactic acid bacteria, including bacteria of the species *Lactobacillus* sp. and *Streptococcus thermophilus*, are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product. Such cultures are in general referred to as "starter cultures" or "starters".

The inventors of the present invention have surprisingly discovered a method for obtaining a composition comprising allolactose by applying one or more glucose-deficient lactic acid bacteria strains, wherein the glucose-deficiency of said strains is caused by a mutation in the DNA sequence of the glcK gene encoding a glucokinase protein it was surprisingly possible to obtain allolactose.

Thus, one aspect of the present invention relates to a method for producing a composition comprising allolactose, said method comprising the steps:

a) inoculating a substrate comprising lactose with one or more glucose-deficient lactic acid bacteria strains, wherein the glucose-deficiency of said strains is caused by a mutation in the DNA sequence of the glcK gene encoding a glucokinase protein; and
b) fermenting said inoculated substrate to obtain a composition comprising allolactose.

The term "resistant to 2-deoxyglucose" herein in relation to *L. bulgaricus* is defined by that a particular mutated bacterial strain has the ability to grow to a colony when streaked on a plate of M17 medium containing 20 mM 2-deoxyglucose after incubation at 40° C. for 20 hours. The presence of 2-deoxyglucose in the culture medium will prevent the growth of non-mutated strains while the growth of the mutated strains is not affected or not affected significantly. Thus, for selection purposes 2-deoxyglucose can be applied in the selection process.

The terms "galactose-positive strain", "gal-positive strain", or "gal+ strain" in the present context are defined as a strain which can metabolize galactose/grow on galactose/utilize galactose for growth. Galactose may be available from hydrolysis of lactose or from transport of galactose into the cell.

The terms "galactose-fermenting strain" or "gal-fermenting strain" in the present context are defined as a strain that reduces pH by a value of at least 1.0 after 16 hours incubation at 37° C. in M17 with 2% galactose added as sole carbohydrate, when inoculated in an amount of at least $10^4$ cells/ml.

Galactokinase encoded by the galK gene is an enzyme of the Leloir pathway for galactose metabolism that converts α-galactose to galactose-1-phosphate.

The term "the mutation inactivates the glucokinase protein" as used herein refers to a mutation which results in an "inactivated glucokinase protein", a glucokinase protein which, if present in a cell, is not able to exert its normal function as well as mutations which prevent the formation of the glucokinase protein or result in degradation of the glucokinase protein. In particular, an inactivated glucokinase protein is a protein which compared to a functional glucokinase protein is not able to facilitate phosphorylation of glucose to glucose-6-phosphate or facilitates phosphorylation of glucose to glucose-6-phosphate at a significantly reduced rate. The gene encoding such an inactivated glucokinase protein compared to the gene encoding a functional glucokinase protein comprises a mutation in the open reading frame (ORF) of the gene, wherein said mutation may include, but is not limited to, a deletion, a frameshift mutation, introduction of a stop co-don or a mutation which results in an amino acid substitution, which changes the functional properties of the protein, or a promoter mutation that reduces or abolishes transcription or translation of the gene.

The term "functional glucokinase protein" as used herein refers to a glucokinase protein which, if present in a cell, facilitates phosphorylation of glucose to glucose-6-phosphate.

In preferred embodiments the mutation reduces the activity (the rate of phosphorylation of glucose to glucose-6-phosphate) of the glucokinase protein with at least 50%, at least 60%, at least 70%, at least 80%, at least 90%, or at least 95% when compared to a strain not carrying a mutation in the DNA sequence of the glcK gene.

Thus, if the mutation inactivates the encoded glucokinase protein the activity of the protein is reduced with 100% when compared to a *S. thermophilus* strain not carrying a mutation in the DNA sequence of the glcK gene. If on the other hand the mutation has a negative effect on expression of the gene the activity of the glucokinase protein is reduced with at least 50%, at least 60%, at least 70%, at least 80%, at least 90%, or at least 95% when compared to a *S. thermophilus* strain not carrying a mutation in the DNA sequence of the glcK gene.

The glucokinase activity can be determined by the glucokinase enzymatic assays as described by Pool et al. (2006) Metabolic Engineering 8; 456-464.

It may be preferred that the method further comprises the steps of:

c) concentrating the composition comprising allolactose to obtain a composition with an increased amount of allolactose as compared to the composition before concentration.

The concentration in step c) may be performed using filtration such as but not limited to diafiltration, membrane filtration, centrifugation, sedimentation, evaporation and/or chromatography however, any applicable method in the art can be used for this purpose.

Depending on the application of allolactose it may be contemplated that the method further comprises the step of:

d) purifying the composition comprising allolactose to obtain a composition with an increased purity of allolactose as compared to the composition before purification.

Purification may be performed using any known method in the art such as but not limited to diafiltration, membrane filtration, centrifugation, sedimentation, evaporation and/or chromatography.

The composition comprising allolactose obtained by the present invention may be a fermented product, such as a fermented food product and more specifically a fermented dairy product.

In an embodiment the one or more one or more glucose-deficient lactic acid bacteria strains are galactose-positive.

In an embodiment the one or more one or more glucose-deficient lactic acid bacteria strains carry a mutation in the galK gene encoding a galactokinase protein.

In an embodiment the one or more one or more glucose-deficient lactic acid bacteria strains are galactose-fermenting.

It may be preferred that the one or more glucose-deficient lactic acid bacteria strains carries a mutation that reduces or inactivates the transport of glucose into the cell. In a preferred embodiment the lactic acid bacterium is a *Streptococcus thermophilus* (*S. thermophilus* that carries a mutation that reduces or inactivates the transport of glucose into the cell.

The term "a mutation that reduces the transport of glucose into the cell" as used herein refers to a mutation in a gene encoding a protein involved in transport of glucose which results in an accumulation of glucose in the environment of the cell. The level of glucose in the culture medium of a *S. thermophilus* strain or an *L. bulgaricus* strain can readily be measured by methods known to the skilled person.

The term "the mutation inactivates the glucose transporter" as used herein refers to a mutation which results in an "inactivated glucose transporter", a glucose transporter protein which, if present in a cell, is not able to exert its normal function as well as mutations which prevent the formation of the glucose transporter protein or result in degradation of the glucose transporter protein.

The one or more glucose-deficient lactic acid bacteria strains may also carry a mutation in a gene encoding a component of a glucose transporter, wherein the mutation reduces or inactivates the glucose transporter or has a negative effect on expression of the gene.

The term "functional glucose transporter protein" as used herein refers to a glucose transporter protein which, if present in a cell, facilitates transport of glucose over a plasma membrane.

The term "glucose-deficient" is used in the context of the present invention to characterize lactic acid bacteria (LAB) which either partially or completely have lost the ability to use glucose as a source for cell growth or for maintaining cell viability. A respective deficiency in glucose metabolism can for example be caused by a mutation in a gene inhibiting or inactivating expression or activity of the glucokinase protein and/or the glucose transporter protein responsible for glucose uptake.

LAB with a deficiency in glucose metabolism may increase the glucose concentration in a culture medium, when grown on lactose as carbohydrate source. The increase of glucose is caused by glucose secretion of the glucose-deficient LABs. Increase of glucose concentration in a culture medium can be determined by HPLC analysis, for example using a Dionex CarboPac PA 20 3*150 mm column (Thermo Fisher Scientific, product number 060142).

The term "glucose-fermenting" is used in the context of the present invention to characterize LAB which either partially or completely have maintained the ability to use glucose as a source for cell growth or maintaining cell viability.

Thus, the one or more glucose-deficient lactic acid bacteria strains such as *S. thermophilus* stains and/or some *Lactobacillus* strains may be both galactose- and glucose fermenting. If a strain can is capable of fermenting both galactose and glucose it may be preferred that this stain carries a mutation that reduces or inactivates the transport of glucose into the cell. These strains will, when grown on a substrate comprising lactose, not or at least to a lesser extent, transport glucose from the milk source and into the cell to metabolize it—it will, on the other hand, transport lactose into the cell, metabolize it to glucose and galactose, further metabolize the galactose and excrete glucose to the environment thus, further increasing the glucose concentration in the culture medium and thereby also increasing the "intrinsic sweetness" of the product.

Likewise, it may be preferred that the one or more glucose-deficient lactic acid bacteria strains carries a mutation in the DNA sequence encoding the glucose/mannose phosphotransferase system.

In a more specific embodiment, the one or more glucose-deficient lactic acid bacteria strains such as but not limited to a *S. thermophilus* strain carries a mutation in the DNA sequence of the manM gene encoding the PTS Mannose/glucose/fructose subunit IIC (may also be termed $IIC^{Man}$ protein of the glucose/mannose phosphotransferase system and the two is therefor used herein interchangeably), wherein the mutation inactivates the $IIC^{Man}$ protein or has a negative effect on expression of the gene. In preferred embodiments the mutation reduces the transport of glucose into the cell with at least 50%, at least 60%, at least 70%, at least 80%, or at least 90% when compared to a cell without such mutation.

The transport of glucose into the cell can be determined by the glucose uptake assay as described by Cochu et al. (2003) Appl Environ Microbiol 69(9); 5423-5432.

In a further embodiment the one or more glucose-deficient lactic acid bacteria strains, such as but not limited to *S. thermophilus* strain, may produce an amount of allolactose in a milk substrate of at least 0.04% w/w of the milk when inoculated into the milk substrate at a concentration of $10^6$-$10^7$ CFU/ml and grown for 18 h at 43° C. and wherein the milk substrate comprises 4% protein, 1.5% fat and 0.1% added sucrose. The milk substrate is prepared as disclosed in Example 1.

In a further embodiment the one or more glucose-deficient lactic acid bacteria strains, such as but not limited to *S. thermophilus* strain, may produce an amount of allolactose in a milk substrate of at least 0.04% w/w of the milk when inoculated into the milk substrate at a concentration of $10^6$-$10^7$ CFU/ml together with at least one further lactic acid bacteria strain (mixed culture) and grown until pH 4.55 was reached at 43° C. and wherein the milk substrate comprises 4% protein and 1.5% fat. The milk source is prepared as disclosed in Example 2.

In an embodiment the one or more glucose-deficient strains are selected from the group consisting of: *Streptococcus* and *Lactobacillus.*

In another embodiment the *Streptococcus* is *Streptococcus thermophilus.*

In another embodiment *Lactobacillus* is selected from the group consisting of *Lactobacillus delbrueckii* subsp. *bulgaricus*, Lacticaseibacillus *rhamnosus* and *Lactobacillus* helvticus, Lacticaseibacillus *paracasei* subsp. *Paracasei.*

In a preferred embodiment the *Streptococcus* is *Streptococcus thermophilus* and *Lactobacillus* is *Lactobacillus delbrueckii* subsp. *bulgaricus.*

In a preferred embodiment the glucose-deficient *S. thermophilus* is selected from the group consisting of DSM 25850, DSM 26722, DSM 28889, DSM 33719, DSM 32227, and DSM 33762 and a mutant strain derived therefrom, wherein the mutant strain is obtained by using one of the deposited strains as starting material, and wherein the mutant has retained or further improved the lactose fermenting property and/or the glucose secreting property of said deposited strain.

It may be contemplated that the glucose-deficient *Lactobacillus* such as *Lactobacillus delbrueckii* subsp. *bulgaricus* produce an amount of allolactose in 9.5% B-milk of at least 0.04% w/w of the B-milk when inoculated into the 9.5% B-milk at a concentration of $10^6$-$10^7$ CFU/ml and grown at 40° C. for at least 20 hours.

Likewise it may be contemplated that the glucose-deficient *Lactobacillus* such as *Lactobacillus delbrueckii* subsp. *bulgaricus* produce an amount of allolactose in 9.5% B-milk of at least 0.04% w/w of the B-milk when inoculated into the 9.5% B-milk at a concentration of $10^6$-$10^7$ CFU/ml together with at least one further lactic acid bacteria strain (mixed culture) and grown at 40° C. for at least 20 hours.

In the method according to the present invention it may be contemplated that one or more glucose-deficient *S. thermophilus* and/or at least one glucose-deficient *L. bulgaricus* strain is inoculated with at least one non-glucose-deficient *S. thermophilus* strain or at least one non-glucose-deficient *L. bulgaricus* strain in step a) and wherein the glucose-deficiency of said strains is caused by a mutation in the DNA sequence of the glcK gene encoding a glucokinase protein.

In order to obtain the best combination of acidity, taste, texture of a composition such as a dairy product, like yoghurt, a combination of *S. thermophilus* and *L. bulgaricus* is often applied.

As it may be contemplated that the substrate in step a) of the method of the present invention is inoculated with:

i. DSM 25850, DSM 26722, DSM 28889 and DSM 28910 DSM 28910, DSM 32227 and DSM 33762;

ii. DSM 25850, DSM 26722, DSM 28889, DSM 28910 and DSM 33720; or iii. DSM 28910, DSM 32227 and DSM 33719.

Likewise, it may be contemplated that the composition of the present invention comprises:

i. DSM 25850, DSM 26722, DSM 28889 and DSM 28910;

ii. DSM 28910, DSM 32227 and DSM 33762;

iii. DSM 25850, DSM 26722, DSM 28889, DSM 28910 and DSM 33720; or iv. DSM 28910, DSM 32227 and DSM 33719.

Probiotic bacterial strains may be added to the method of the present invention either before or after fermentation. If added before fermentation the probiotic bacterial strain also acts as fermentative bacteria.

The term "probiotic bacteria" refers to viable bacteria which are administered in adequate amounts to a consumer for the purpose of achieving a health-promoting effect in the consumer. Probiotic bacteria are capable of surviving the conditions of the gastrointestinal tract after ingestion and colonize the intestine of the consumer.

It will be appreciated that the *Lactobacillus* genus taxonomy was updated in 2020. The new taxonomy is disclosed in Zheng et al. 2020 and will be cohered to herein if not otherwise indicated. For the purpose of the present invention, the table below presents a list of new and old names of some *Lactobacillus* species relevant to the present invention.

TABLE 1

New and old names of *Lactobacillus* species relevant to the present invention.

| Old Name | New Name |
|---|---|
| *Lactobacillus reuteri* | *Limosilactobacillus reuteri* |
| *Lactobacillus rhamnosus* | *Lacticaseibacillus rhamnosus* |
| *Lactobacillus salivarius* | *Ligilactobacillus salivarius* |
| *Lactobacillus casei* | *Lacticaseibacillus casei* |
| *Lactobacillus paracasei* subsp. *paracasei* | *Lacticaseibacillus paracasei* subsp. *Paracasei* |
| *Lactobacillus plantarum* subsp. *plantarum* | *Lactiplantibacillus plantarum* subsp. *plantarum* |
| *Lactobacillus fermentum* | *Limosilactobacillus fermentum* |
| *Lactobacillus animalis* | *Ligilactobacillus animalis* |
| *Lactobacillus buchneri* | *Lentilactobacillus buchneri* |

TABLE 1-continued

New and old names of *Lactobacillus* species relevant to the present invention.

| Old Name | New Name |
|---|---|
| *Lactobacillus curvatus* | *Latilactobacillus curvatus* |
| *Lactobacillus futsaii* | *Companilactobacillus futsaii* |
| *Lactobacillus sakei* subsp. *sakei* | *Latilactobacillus sakei* subsp. |
| *Lactobacillus pentosus* | *Lactiplantibacillus pentosus* |

In a particular embodiment of the invention the probiotic strain according to the present invention is selected from the group consisting of bacteria of the genus *Lactobacillus*, such as *Lactobacillus acidophilus, Lacticaseibacillus paracasei, Lacticaseibacillus rhamnosus, Lacticaseibacillus casei, Lactobacillus delbrueckii, Lactobacillus lactis, Lactiplantibacillus plantarum, Limosilactobacillus reuteri* and *Lactobacillus johnsonii*, the genus *Bifidobacterium*, such as the *Bifidobacterium longum, Bifidobacterium adolescentis, Bifidobacterium bifidum, Bifidobacterium breve, Bifidobacterium animalis* subsp. *lactis, Bifidobacterium dentium, Bifidobacterium catenulatum, Bifidobacterium angulatum, Bifidobacterium magnum, Bifidobacterium pseudocatenulatum* and *Bifidobacterium infantis*, and the like.

In a particular embodiment of the invention, the probiotic *Lactobacillus* strain is selected from the group consisting of *Lactobacillus acidophilus, Lacticaseibacillus paracasei, Lacticaseibacillus rhamnosus, Lactobacillus casei, Lactobacillus delbrueckii, Lactobacillus lactis, Lactiplantibacillus plantarum, Limosilactobacillus reuteri* and *Lactobacillus johnsonii*.

In a particular embodiment of the invention, the probiotic strain is *Lactobacillus acidophilus* (LA-5®) deposited as DSM 13241.

In a particular embodiment of the invention, the probiotic *Lactobacillus* strain is selected from the group consisting of a Lacticaseibacillus *rhamnosus* strain and a Lacticaseibacillus *paracasei* strain. In a particular embodiment of the invention, the probiotic strain is Lacticaseibacillus *rhamnosus* strain LGG® deposited as ATCC 53103. In a particular embodiment of the invention, the probiotic strain is *Lacticaseibacillus paracasei* strain CRL 431 deposited as ATCC 55544.

In a particular embodiment of the invention, the probiotic *Bifidobacterium* strain is selected from the group consisting of *Bifidobacterium longum, Bifidobacterium adolescentis, Bifidobacterium bifidum, Bifidobacterium breve, Bifidobacterium animalis* subsp. *lactis, Bifidobacterium dentium, Bifidobacterium catenulatum, Bifidobacterium angulatum, Bifidobacterium magnum, Bifidobacterium pseudocatenulatum* and *Bifidobacterium infantis*. In a particular embodiment of the invention, the probiotic *Bifidobacterium* probiotic strain is *Bifidobacterium animalis* subsp. *lactis* BB-12® deposited as DSM 15954.

Depending on the nature of the composition comprising allolactose it may be preferred that the substrate comprising lactose is an animal and/or plant derived substrate. It may be preferred that the substrate comprising lactose is dairy substrate such as a milk substrate.

The term "milk" is to be understood as the lacteal secretion obtained by milking any mammal, such as cows, sheep, goats, buffaloes or camels. In a preferred embodiment, the milk is cow's milk. The term milk also includes protein/fat solutions made partly or completely of plant materials.

Milk constituents may be replaced partly with plant material(s), for example, using planted-based milks derived from legumes (such as soybeans), nuts (such as coconut), cereals (such as oat).

The term "legume" refers to any plant belonging to the family Fabaceae. Fabaceae is a large and economically important family of flowering plants, which is commonly known as the legume family, pea family, bean family or pulse family. A variety of different legumes can be consumed. Legumes typically have a pod or hull that opens along two sutures when the seeds of the legume are ripe.

The term "nuts" as used herein can be true nuts from tree or shrubs or culinary nuts which may be drupaceous nuts or seeds that are nut-like. In botanical terms, a nut is a dry one-seeded fruit which is indehiscent (i.e., it does not split open along a definite seam at maturity). Culinary nuts are those that are not botanically qualified as nuts, but that have a similar appearance and culinary role. Many culinary nuts are seeds of a drupe, referred herein as drupaceous nuts. A drupe is an indehiscent fruit in which an outer fleshy part surrounds a single shell (the pit or stone) hardened endocarp with a seed inside. Drupaceous nuts are seed of drupes.

The term "cereal" refers to both true cereal and pseudocereal. True cereal refers to the seeds of plants of the Poaceae family. Pseudocereal are seed of plants which do not belong to Poaceae family but are used in much the same way as cereals.

If the substrate is a fully plant derived substrate lactose is added so as to obtain a substrate comprising lactose. Lactose may be obtained from a side-stream in the dairy industry.

The term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder or the milk substrate may originate from a plant material. Preferably, at least part of the protein in the milk substrate is (i) proteins naturally occurring in mammalian milk, such as casein or whey protein or (ii) proteins naturally occurring in plant milk. However, part of the protein may be proteins which are not naturally occurring in milk.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

Fermentation processes to be used in production of fermented milk products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a fermented product such as a dairy or dairy analogue product in solid or liquid form (fermented milk product).

The composition comprising lactose may be a fermented product such as a fermented dairy product selected from the group consisting of yoghurt (set, stirred, or drinking), buttermilk, sour milk, sour cream, kefir, quark, tvarog and cheese. In an embodiment the cheese may be selected from the group consisting of fresh cheese, cream cheese or pasta filata.

Depending on the product and the intended consumer the composition comprising allolactose may further comprises an ingredient selected from the group consisting of a fruit concentrate, a syrup, a probiotic bacterial strain or culture, a coloring agent, a thickening agent, a flavoring agent, a preserving agent and mixtures thereof.

Likewise, an enzyme may added to the substrate comprising lactose before, during and/or after the fermenting, the enzyme being selected from the group consisting of an enzyme able to crosslink proteins, transglutaminase, an aspartic protease, lactase, chymosin, rennet and mixtures thereof.

The composition comprising allolactose such as a fermented product comprising allolactose may be in the form of a stirred type product, a set type product, or a drinkable product.

An aspect of the invention relates to a composition comprising allolactose obtained by the method according to the present invention.

In an aspect the invention relates to a composition comprising at least 0.04% w/w, at least 0.06% w/w, at least 0.08% w/w, at least 0.10% w/w, at least 0.15% w/w, at least 0.20% w/w, at least 0.25% w/w, at least 0.30% w/w, at least 0.35% w/w, at least 0.40% w/w, at least 0.45% w/w, at least 0.50% w/w, at least 0.55% w/w, at least 0.60% w/w, at least 0.65% w/w, at least 0.70% w/w, at least 0.75% w/w, at least 0.80% w/w, at least 0.85% w/w, at least 0.90% w/w, at least 0.95% w/w, at least 1% w/w, or in the range from 0.04% w/w-1% w/w, from 0.06% w/w-0.95% w/w, from 0.08% w/w-0.90% w/w, from 0.10% w/w-0.85% w/w, from 0.15% w/w-0.80% w/w, from 0.20% w/w-0.75% w/w, from 0.25% w/w-0.70% w/w, from 0.30% w/w-0.65% w/w, from 0.35% w/w-0.60% w/w, from 0.40% w/w-0.55% w/w, or from 0.45% w/w-0.50% w/w allolactose and wherein said composition further comprises one or more glucose-deficient lactic acid bacteria strains, wherein the glucose-deficiency of said strains is caused by a mutation in the DNA sequence of the glcK gene encoding a glucokinase protein.

The composition of the present invention may be provided in several forms. It may be a powder, pellets or tablets. It may be a frozen form, dried form, freeze dried form, or liquid form. Thus, in one embodiment the composition is in frozen, dried, freeze-dried or liquid form.

The composition of the present invention may additionally comprise cryoprotectants, lyoprotectants, antioxidants, nutrients, fillers, flavorants or mixtures thereof. The composition preferably comprises one or more of cryoprotectants, lyoprotectants, antioxidants and/or nutrients, more preferably cryoprotectants, lyoprotectants and/or antioxidants and most preferably cryoprotectants or lyoprotectants, or both. Use of protectants such as cryoprotectants and lyoprotectantare known to a skilled person in the art. Suitable cryoprotectants or lyoprotectants include mono-, di-, tri- and polysaccharides (such as glucose, mannose, xylose, lactose, sucrose, trehalose, raffinose, maltodextrin, starch and gum arabic (acacia) and the like), polyols (such as erythritol, glycerol, inositol, mannitol, sorbitol, threitol, xylitol and the like), amino acids (such as proline, glutamic acid), complex substances (such as skim milk, peptones, gelatin, yeast extract) and inorganic compounds (such as sodium tripolyphosphate).

In one embodiment, the composition according to the present invention may comprise one or more cryoprotective agent(s) selected from the group consisting of inosine-5'-monophosphate (IMP), adenosine-5'-monophosphate (AMP), guanosine-5'-monophosphate (GMP), uranosine-5'-monophosphate (UMP), cytidine-5'-monophosphate (CMP), adenine, guanine, uracil, cytosine, adenosine, guanosine, uridine, cytidine, hypoxanthine, xanthine, hypoxanthine, orotidine, thymidine, inosine and a derivative of any such compounds. Suitable antioxidants include ascorbic acid, citric acid and salts thereof, gallates, cysteine, sorbitol, mannitol, maltose. Suitable nutrients include sugars, amino acids, fatty acids, minerals, trace elements, vitamins (such as vitamin B-family, vitamin C). The composition may optionally comprise further substances including fillers (such as lactose, maltodextrin) and/or flavorants.

In one embodiment of the invention the cryoprotective agent is an agent or mixture of agents, which in addition to its cryoprotectivity has a booster effect.

The expression "booster effect" is used to describe the situation wherein the cryoprotective agent confers an increased metabolic activity (booster effect) on to the thawed or reconstituted culture when it is inoculated into the medium to be fermented or converted. Viability and metabolic activity are not synonymous concepts. Commercial frozen or freeze-dried cultures may retain their viability, although they may have lost a significant portion of their metabolic activity e.g. cultures may lose their acid-producing (acidification) activity when kept stored even for shorter periods of time. Thus, viability and booster effect have to be evaluated by different assays. Whereas viability is assessed by viability assays such as the determination of colony forming units, booster effect is assessed by quantifying the relevant metabolic activity of the thawed or reconstituted culture relative to the viability of the culture. The term "metabolic activity" refers to the oxygen removal activity of the cultures, its acid-producing activity, i. e. the production of e. g. lactic acid, acetic acid, formic acid and/or propionic acid, or its metabolite producing activity such as the production of aroma compounds such as acetaldehyde, (a-acetolactate, acetoin, diacetyl and 2,3-butylene glycol (butanediol)).

In one embodiment the composition of the invention contains or comprises from 0.2% to 20% of the cryoprotective agent or mixture of agents measured as % w/w of the material. It is, however, preferable to add the cryoprotective agent or mixture of agents at an amount which is in the range from 0.2% to 15%, from 0.2% to 10%, from 0.5% to 7%, and from 1% to 6% by weight, including within the range from 2% to 5% of the cryoprotective agent or mixture of agents measured as % w/w of the frozen material by weight. In a preferred embodiment the culture comprises approximately 3% of the cryoprotective agent or mixture of agents measured as % w/w of the material by weight. The amount of approximately 3% of the cryoprotective agent corresponds to concentrations in the 100 mM range. It should be recognized that for each aspect of embodiment of the invention the ranges may be increments of the described ranges.

In the present context the term "from x % to y %" means to include the end-points, thus equal to the term "from and including x % to and including y %"

In a further aspect, the composition of the present invention contains or comprises an ammonium salt (e.g. an ammonium salt of organic acid (such as ammonium formate and ammonium citrate) or an ammonium salt of an inorganic acid) as a booster (e.g. growth booster or acidification booster) for bacterial cells, such as cells belonging to the species *S. thermophilus*, e.g. (substantial) urease negative bacterial cells. The term "ammonium salt", "ammonium formate", etc., should be understood as a source of the salt or a combination of the ions. The term "source" of e.g. "ammonium formate" or "ammonium salt" refers to a compound or mix of compounds that when added to a culture of cells, provides ammonium formate or an ammonium salt. In some embodiments, the source of ammonium releases ammonium into a growth medium, while in other embodiments, the ammonium source is metabolized to produce ammonium. In some preferred embodiments, the ammonium source is exogenous. In some particularly preferred embodiments, ammonium is not provided by the dairy substrate. It should of course be understood that ammonia may be added instead of ammonium salt. Thus, the term ammonium salt comprises ammonia ($NH3$), $NH4OH$, $NH4+$, and the like.

In one embodiment the composition of the invention may comprise thickener and/or stabilizer, such as pectin (e.g. HM pectin, LM pectin), gelatin, CMC, Soya Bean Fiber/Soya Bean Polymer, starch, modified starch, carrageenan, alginate, and guar gum In one embodiment wherein the microorganism produces a polysaccharide (such as EPS) which causes a high/ropy texture in the acidified milk product the acidified milk product is produced substantially free, or completely free of any addition of thickener and/or stabilizer, such as pectin (e.g. HM pectin, LM pectin), gelatin, CMC, Soya Bean Fiber/Soya Bean Polymer, starch, modified starch, carrageenan, alginate, and guar gum. By substantially free should be understood that the product comprises from 0% to 20% (w/w) (e.g. from 0% to 10%, from 0% to 5% or from 0% to 2% or from 0% to 1%) thickener and/or stabilizer.

Needless to say, all embodiments disclosed in respect of the method of the present invention are equally applicable to aspects and embodiments of the composition of the present invention.

Another aspect of the present invention relates to the use of one or more glucose-deficient strains for producing a composition comprising allolactose, wherein the glucose-deficiency of said strains is caused by a mutation in the DNA sequence of the glcK gene encoding a glucokinase protein.

In a further aspect the invention relates to the use of one or more glucose-deficient strains for increasing the content of allolactose in a composition, wherein the glucose-deficiency of said strains is caused by a mutation in the DNA sequence of the glcK gene encoding a glucokinase protein.

Needless to say, all embodiments disclosed in respect of the method of the present invention and the composition of the present invention are equally applicable to aspects and embodiments of the various uses of the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The listing or discussion of an apparently prior published document in this specification should not necessarily be taken as an acknowledgement that the document is part of the state of the art or is common general knowledge.

Preferences, options and embodiments for a given aspect, feature or parameter of the invention should, unless the context indicates otherwise, be regarded as having been disclosed in combination with any and all preferences, options and embodiments for all other aspects, features and parameters of the invention. This is especially true for the description of the fat encapsulated microbial culture and all its features, which may readily be part of the final composition or product obtained by the method as described herein. Embodiments and features of the present invention are also outlined in the following items.

Items

A1. A method for producing a composition comprising allolactose, said method comprising the steps:

a) inoculating a substrate comprising lactose with one or more glucose-deficient lactic acid bacteria strains, wherein the glucose-deficiency of said strains is caused by a mutation in the DNA sequence of the glcK gene encoding a glucokinase protein; and b) fermenting said inoculated substrate to obtain a composition comprising allolactose.

A2. The method according to item A1 further comprising the step:

c) concentrating the composition comprising allolactose to obtain a composition with an increased amount of allolactose as compared to the composition before concentration.

A3. The method according to any one of items A1 or A2 further comprising the step:

d) purifying the composition comprising allolactose to obtain a composition with an increased purity of allolactose as compared to the composition before purification.

A4. The method according to any one of the preceding items, wherein the composition comprising allolactose is a food product and more specifically a fermented dairy product.

A5. The method according to any one of the preceding items, wherein step c) is performed using filtration such as but not limited to diafiltration, membrane filtration, centrifugation, sedimentation, evaporation and/or chromatography.

A6. The method according to any one of the preceding items, wherein the one or more strains are galactose-positive.

A7. The method according to any one of the preceding items, wherein the one or more strains carry a mutation in the galK gene encoding a galactokinase protein.

A8. The method according to any one of the preceding items, wherein the one or more strains are galactose-fermenting.

A9. The method according any one of the preceding items, wherein the one or more strains carries a mutation in a gene that reduces or inactivates the transport of glucose into and/or out of the cell.

A10. The method according to the preceding items, wherein the gene encodes a component of a glucose transporter system.

A11. The method according to the preceding items, wherein the glucose transporter system is the glucose/mannose phosphotransferase system.

A12. The method according to any of the preceding items, wherein the one or more strains produce an amount of allolactose in a milk substrate of at least 0.04% w/w of the milk when inoculated into the milk substrate at a concentration of $10^6$-$10^7$ CFU/ml and grown for 18 h at 43° C. and wherein the milk substrate comprises 4% protein, 1.5% fat and 0.1% added sucrose.

A13. The method according to any one of the preceding items wherein the one or more glucose-deficient strains are selected from the group consisting of *Streptococcus* and *Lactobacillus*.

A14. The method according to the preceding items, wherein *Streptococcus* is *Streptococcus thermophilus* and *Lactobacillus* is *Lactobacillus delbrueckii* subsp. *bulgaricus*.

A15. The method according to any one of the preceding items, wherein the *Streptococcus thermophilus* strain is selected from the group consisting of DSM 25850, DSM 26722, DSM 28889, DSM 33719, DSM 32227, and DSM 33762 and a mutant strain derived thereof, wherein the mutant strain is obtained by using one of the deposited strains as starting material, and wherein the mutant has retained or further improved the lactose fermenting property and/or the glucose secreting property of said deposited strain.

A16. The method according to any one of the preceding items, wherein one or more glucose-deficient *S. thermophilus* and/or at least one glucose-deficient *L. bulgaricus* strain is inoculated with at least one non-glucose-deficient *S. thermophilus* strain or at least one non-glucose-deficient *L. bulgaricus* strain in step a) and wherein the glucose-deficiency of said strains is caused by a mutation in the DNA sequence of the glcK gene encoding a glucokinase protein.

A17. The method according to any one of the preceding items, wherein the substrate in step a) of claim 1 in inoculated with:

i. DSM 25850, DSM 26722, DSM 28889 and DSM 28910 DSM 28910, DSM 32227 and DSM 33762;

ii. DSM 25850, DSM 26722, DSM 28889, DSM 28910 and DSM 33720; or iii. DSM 28910, DSM 32227 and DSM 33719.

A18. The method according to any of the preceding items, wherein the amount of allolactose in the composition is at least 0.04% w/w.

A19. The method according to any of the preceding items, wherein the substrate comprising lactose is an animal and/or plant derived substrate.

A20. The method according to any of the preceding items, wherein the substrate comprising lactose is dairy substrate.

A21. The method according to any of the preceding items, wherein the fermented dairy product selected from the group consisting of yoghurt (set, stirred, or drinking), buttermilk, sour milk, sour cream, kefir, quark, tvarog and cheese.

A22. The method according to any of the preceding items, wherein cheese is selected from the group consisting of f fresh cheese, cream cheese or pasta filata.

A23. The method according to any one of the preceding items, wherein the product comprising allolactose such as the fermented fresh dairy product further comprises an ingredient selected from the group consisting of a fruit concentrate, a syrup, a probiotic bacterial strain or culture, a coloring agent, a thickening agent, a flavoring agent, a preserving agent and mixtures thereof.

A24. The method according to any one of the preceding items, wherein an enzyme is added to the substrate comprising lactose before, during and/or after the fermenting, the enzyme being selected from the group consisting of an enzyme able to crosslink proteins, transglutaminase, an aspartic protease, chymosin, rennet and mixtures thereof.

A25. The method according to any one of any one of the preceding items, wherein the fermented product is in the form of a stirred type product, a set type product, or a drinkable product.

B1. A composition comprising allolactose obtained by the method according to any one of items A12-A25.

C1. A composition comprising at least 0.04% w/w allolactose, wherein said composition further comprises one or more glucose-deficient lactic acid bacteria strains, wherein the glucose-deficiency of said strains is caused by a mutation in the DNA sequence of the glcK gene encoding a glucokinase protein.

D1. Use of one or more glucose-deficient strains for producing a composition comprising allolactose, wherein the glucose-deficiency of said strains is caused by a mutation in the DNA sequence of the glcK gene encoding a glucokinase protein.

E1. Use of one or more glucose-deficient strains for increasing the content of allolactose in a composition, wherein the glucose-deficiency of said strains is caused by a mutation in the DNA sequence of the glcK gene encoding a glucokinase protein.

Deposits and Expert Solutions

The applicant requests that a sample of the deposited microorganisms stated in the table below may only be made available to an expert, until the date on which the patent is granted.

TABLE 2

Deposits made at a Depositary institution having acquired the status of international depositary authority under the Budapest Treaty on the International Recognition of the Deposit of Microorganisms for the Purposes of Patent Procedure: *Leibniz Institute DSMZ-German Collection of Microorganisms and Cell Cultures* Inhoffenstr. 7B, 38124 Braunschweig, Germany.

| Strain | Accession No. | Deposit date |
|---|---|---|
| *Streptococcus thermophilus* | DSM 33719 | 2020 Nov. 26 |
| *Streptococcus thermophilus* | DSM 33762 | 2021 Jan. 19 |
| *Streptococcus thermophilus* | DSM 33720 | 2020 Nov. 26 |

EXAMPLES

Example 1—Production of Allolactose by Single Strains

All cultures tested were provided as frozen pellets from Chr. Hansen.

Milk with 4% protein, 1.5% fat and 0.1% added sucrose was prepared by mixing skimmed milk powder, semi skimmed milk and sucrose until fully hydrated. The milk was pasteurized and poured into 200 mL bottles.

Before the inoculation, cultures were melted, pre-diluted in milk according to the recommendation from Chr. Hansen. Cultures were added to the milk in the inoculation rate of 0.01% (corresponding to CFU of $10^6$-$10^7$). Inoculated milk was incubated at 43° C. for 18 hours, cooled to 6° C., and sampled for chemical analysis. Fermented milk samples for carbohydrate analysis were prepared by weighing 1 g of sample into a 10 mL centrifuge tubes, followed by addition of 2 mL of ice cold 96% ethanol. Samples were mixed on the vortex and stored at −50° C. until analysis.

Concentrations of fructose, galactose, glucose, sucrose, lactose and allolactose were measured by High-Performance Anion-Exchange chromatography with Pulsed Amperometric Detection (HPAE-PAD). Samples were quenched with EtOH 96%. The analytes (i.e. carbohydrates) were extracted from the sample and proteins got deproteinated. The samples were further diluted to fit into the dynamic range of the quantification. Fucose was added as an internal standard. The diluted samples were analyzed on a Dionex ICS-5000, 6000 or Integrion system (Thermo Fischer Scientific, Waltham (MA), USA) using an analytical anion-exchange column and a pulsed amperometric detector (PAD). For quantification an 8-point calibration curve was used. Concentrations were calculated based on the chromatographic peak heights after normalizing to the internal standard (fucose).

TABLE 3

Allolactose produced by various single strains and Reference cultures. The results are averages of two independent samples. Limit of detection (LoD).

| Culture | Presence of a glucose-deficient strain | Concentration of Allolactose (mg/g) |
|---|---|---|
| DSM 25850 | + | 3.4 |
| DSM 26722 | + | 6.0 |
| DSM 28889 | + | 1.9 |
| DSM 32227 | + | 5.4 |
| DSM 33719 | + | 1.0 |
| DSM 17876 | − | <LoD |
| DSM 18111 | − | <LoD |
| DSM 22935 | − | <LoD |
| DSM 24090 | − | <LoD |
| DSM 32826 | − | <LoD |
| DSM 33720 | − | <LoD |
| Premium 1.0 | − | <LoD |
| Culture 1 | + | 7.2 |

Results clearly show that the presence of a glucose-deficient strain in a culture produce measurable levels of allolactose, whereas absence of a glucose-deficient strain in a culture does not produce allolactose.

Example 2—Allolactose Produced by Cultures of the Invention

TABLE 4

List of cultures used in the experiment

| Culture | Glu-deficient strain comprised | DSM 15757 | DSM 16404 | DSM 16731 | DSM 19216 | DSM 29110 | DSM 38040 |
|---|---|---|---|---|---|---|---|
| Premium 1.0 | − | | | | | | |
| Culture 1 | + | | | | | | |
| Blend A | + | + | + | + | | | + |
| Blend B | + | + | + | + | | | + |
| Blend C | + | | | | + | + | |

Cultures were inoculated according to their recommended use and inoculation rate (0.2 U/L) to milk base prepared from semi skimmed milk, skimmed milk powder, and sucrose blended to contain 4.0% protein, 1.5% fat and different levels of sucrose (see Table 2). Inoculated milk samples were incubated at 43° C. until they reached a pH of 4.55, after which they were cooled to 6° C. and sampled for chemical analysis. Samples were prepared and the concentration of glucose, galactose, fructose, sucrose, lactose was measured as disclosed in Example 1.

TABLE 5

Carbohydrate content (mg/g) in the fermented milk samples produced with different cultures. Results are averages of two independent samples. Limit of Detection (LoD).

| Culture | Added Sucrose | Glu | Gal | Fru | Suc | Lac | Allo |
|---|---|---|---|---|---|---|---|
| Premium 1.0 | 0% | 0.65 | 7.22 | <LoD | <LoD | 38.60 | 0.33 |
| Premium 1.0 | 6.0% | 1.10 | 6.64 | <LoD | 61.96 | 38.21 | <LoD |
| Culture 1 | 0.1% | 15.80 | 13.92 | <LoD | <LoD | 6.31 | 7.37 |
| Blend A | 0.1% | 6.63 | 9.13 | <LoD | <LoD | 18.27 | 7.66 |
| Blend A | 5.0% | 9.06 | 8.44 | 2.09 | 45.17 | 24.40 | 8.49 |
| Blend B | 0.1% | 6.50 | 9.01 | 0.26 | <LoD | 17.03 | 7.89 |
| Blend B | 5.0% | 9.63 | 8.90 | 2.22 | 43.37 | 21.54 | 9.01 |

The results clearly show higher presence of allolactose in samples produced with cultures comprising a glucose-deficient strain as compared to a control culture Premium 1.0 not comprising a glucose-deficient strain.

Example 3—Milk Acidification and Carbohydrate Analysis of Milk Fermented with Different Combinations and Ratios of Strains

TABLE 6

Strain combinations for cultures of the invention. All cultures comprise strains with a mutated glcK.

| | Culture 1 | Culture 2 | Culture 3 | Culture 4 |
|---|---|---|---|---|
| DSM 25850 | + | | + | |
| DSM 26722 | + | | + | |
| DSM 28889 | + | | + | |
| DSM 28910 | + | + | + | + |
| DSM 32227 | | + | | + |
| DSM 33719 | | | | + |
| DSM 33720 | | | + | |
| DSM 33762 | | + | | |

Two different milk bases were produced prior to fermentation. Skimmed milk powder and sucrose were added to the milk with subsequent 2-hour hydration without stirring, where after homogenization and pasteurization for 1 minute at >=80° C. was conducted. Milk base 1 contained 0.1% sucrose, 4% protein (adjusted with skimmed milk powder) and 1.5% fat (1.5% fat milk adjusted with 9% cream). Milk base 2 contained 5% sucrose, 4% protein (adjusted with skimmed milk powder) and 1.5% fat (1.5% fat milk adjusted with 9% cream).

The milk bases were transferred into 200 mL baby bottles. The bottles were inoculated with a 100× liquid dilution prepared from frozen pellets (F-DVS) dissolved in B-milk. For each strain, an individual dilution was prepared. In order to create a blend, several strains were inoculated into 1 CINAC bottle in differing ratios and volumes. The final inoculation rate of the blends corresponded 1E+6-1E+8 CFU/mL.

Apart from DSM 33762 used in Culture 2, all strains were inoculated from a first dilution created from F-DVS. For preparation of the DSM 33762 inoculation material, 1 mL M17 B-K medium with 4% sucrose and casein peptone in excess was inoculated with a scrap of DSM 33762 and incubated aerobically at 43° C. for at least 18 hours.

The inoculated bottles were placed into a water bath and heated to 43° C. pH was monitored at 43° C. according to prior art using CINAC hardware and software until the blends reached the final pH of 4.55.

Fermented milk samples were prepared for allolactose analysis by weighing 1 g+/−0.5 g into 10 mL centrifuge tubes. 2 mL ice cold 96% ethanol was added, the samples where whirly-mixed and placed at −50° C. until analyzed. The concentration of allolactose was analyzed according to the method disclosed in Example 1.

TABLE 7

Fermentation time and allolactose content obtained with Cultures of the invention.

| Milk base 1 | Fermentation time to target pH 4.55 (hours) | Concentration of Allolactose (mg/g) |
|---|---|---|
| Premium 1.0 | 5.5 | 0 |
| YF-L904 | 5.4 | 0 |
| Culture 1 | 11.1 | 7.1 |
| Culture 3 (Blend 1-8) | 7.9-8.6 | 6.0-7.5 |
| Culture 4 (Blend 1-6) | 9-12 | 7.2-9.2 |

The trial was conducted in milk base 1. The results for Culture 3 and Culture 4 are obtained from different blends, i.e. e.g. each of the 8 Culture 3 blends comprise the same strains but in a different amount and ratios.

The fermentation time and the concentration of allolactose are dependent on the culture. Allolactose is produced by cultures of the invention, Culture 1, Culture 3, and Culture 4 whereas no allolactose could be detected when using the yogurt cultures Premium 1.0 and YF-L904 both sold by Chr. Hansen A/S. Different ratios of strains in the blend variants can lead to variation in i.e. fermentation times or allolactose levels. Thus, the composition of a culture and a blend can accordingly be adjusted to address the specific needs required in the final fermented product.

TABLE 8

Fermentation time and allolactose content obtained with Cultures of the invention in two different milk bases.

| | Fermentation time to target pH 4.55 (hours) | Concentration of Allolactose (mg/g) |
|---|---|---|
| Milk base 1: | | |
| Culture 1 | 12 | 5 |
| Culture 2 (Blend 1-6) | 8-11 | 4-6 |
| Milk base 2: | | |
| Culture 1 | 14 | 7 |
| Culture 2 (Blend 1-6) | 8-10 | 3-4 |

The table shows the results obtained with Culture 1 and Culture 2 (Blend 1-6). Blend 1-6 are six blend variations comprising the same strains but in different amounts and ratios. It can be seen that the fermentation time and the concentration of allolactose is dependent on the culture and the milk base.

Example 4—Different Ratio of Strains in a Culture Changes the Properties of a Fermented Milk Product Fermented milk was produced and analyzed as described in Example 3.

TABLE 9

Composition of Culture 4 variants (% of Total)

| | C4 Variant S03b | C4 Variant S03 | C4 Variant P07 |
|---|---|---|---|
| DSM 33719 | 5 | 10 | 20 |
| DSM 33720 | 80 | 75 | 90 |
| DSM 28910 | 5 | 5 | 5 |
| TOTAL | 100 | 100 | 125 |

TABLE 10

Fermentation time and allolactose content obtained with Culture 4 variants in Milk base 1

| Milk base 1 | Fermentation time to target pH 4.60 (hours) | Concentration of Allolactose (mg/g) |
|---|---|---|
| Culture 1 | 11.0 | 7.4 |
| Culture 4 - S03b | 11.5 | 8.4 |
| Culture 4 - S03 | 10.7 | 8.5 |
| Culture 4 - P07 | 10.2 | 8.8 |

TABLE 11

Fermentation time and allolactose content obtained with Culture 4 variants in Milk base 2.

| Milk base 2 | Fermentation time to target pH 4.60 (hours) | Concentration of Allolactose (mg/g) |
|---|---|---|
| Culture 1 | 12.6 | 8.4 |
| Culture 4 - S03b | 12.0 | 5.9 |
| Culture 4 - S03 | 9.0 | 4.6 |
| Culture 4 - P07 | 8.6 | 4.1 |

Different ratios of strains in Culture 4 variants (S03b, S03 and P07) lead to variation in fermentation time and concentration of allolactose. In milk base 1, the Culture 4 variants are producing higher allolactose levels compared to Culture 1. This is however reverted in milk base 2, where the Culture 4 variants produced higher allolactose levels compared to Culture 1. The level of produced allolactose is dependent on the culture composition and milk base.

The invention claimed is:

1. A method for producing a composition comprising allolactose, said method comprising:

(a) inoculating a substrate comprising lactose with one or more glucose-deficient lactic acid bacteria strains, wherein said one or more glucose-deficient lactic acid bacteria strains have a mutation in a glcK gene encoding a glucokinase protein thereby causing the glucose deficiency; and (b) fermenting said inoculated substrate to obtain a composition comprising allolactose; wherein at least one of the one or more glucose-deficient lactic acid bacteria strains is selected from a group consisting of *Streptococcus thermophilus* strains deposited at DSMZ under accession number DSM 33719, DSM 33762, and a mutant strain derived from either thereof, wherein the mutant strain is obtained by using one of the deposited strains as starting material, and wherein the mutant has retained or further improved the lactose fermenting property and/or the glucose secreting property of said deposited strain.

2. The method according to claim 1, further comprising:

(c) concentrating the composition comprising allolactose to obtain a composition with an increased amount of allolactose as compared to the composition before concentration.

3. The method according to claim 1, wherein the one or more glucose-deficient strains are galactose-positive.

4. The method according to claim 1, wherein the one or more glucose-deficient strains also has a mutation in a galK gene encoding a galactokinase protein.

5. The method according to claim 1, wherein the one or more glucose-deficient strains are galactose-fermenting.

6. The method according to claim 1, wherein the one or more glucose-deficient strains also has a mutation in a gene that reduces or inactivates transport of glucose into and/or out of a cell of the strain.

7. The method according to claim 6, wherein the gene that reduces or inactivates transport of glucose encodes a component of a glucose transporter system.

8. The method according to claim 1, wherein the one or more glucose-deficient strains are selected from *Streptococcus* strains and *Lactobacillus* strains.

9. The method according to claim 1, wherein the substrate in step (a) is inoculated with:

(i). strains deposited at DSMZ under accession numbers DSM 28910, DSM 32227 and DSM 33762; or (ii). strains deposited at DSMZ under accession numbers DSM 28910, DSM 32227 and DSM 33719.

10. The method according to claim 1, wherein the amount of allolactose in the composition is at least 0.04% w/w.

11. A composition comprising allolactose obtained by the method according to claim 1.

12. A composition comprising at least 0.04% w/w allolactose, wherein said composition further comprises one or more glucose-deficient lactic acid bacteria strains, wherein said one or more glucose-deficient strains have a mutation in a glcKL gene encoding a glucokinase protein causing the glucose deficiency, wherein at least one of the one or more glucose-deficient lactic acid bacteria strains is selected from a group consisting of *Streptococcus thermophilus* strains deposited at DSMZ under accession number DSM 33719, DSM 33762, and a mutant strain derived from either thereof, wherein the mutant strain is obtained by using one of the deposited strains as starting material, and wherein the mutant has retained or further improved the lactose fermenting property and/or the glucose secreting property of said deposited strain.

* * * * *